(12) United States Patent
Wang

(10) Patent No.: US 11,628,585 B1
(45) Date of Patent: Apr. 18, 2023

(54) TELESCOPIC ASSEMBLY AND OCCLUSION MECHANISM

(71) Applicant: Dongguan Mi Mao Electronic Technology Co., Ltd., Dongguan (CN)

(72) Inventor: Qinling Wang, Heyuan (CN)

(73) Assignee: Dongguan Mi Mao Electronic Technology Co., Ltd., Dongguan (CN)

( * ) Notice: Subject to any disclaimer, the term of this patent is extended or adjusted under 35 U.S.C. 154(b) by 0 days.

(21) Appl. No.: 17/956,602

(22) Filed: Sep. 29, 2022

(51) Int. Cl.
*B26D 7/02* (2006.01)
*A61B 17/12* (2006.01)
*F16H 25/12* (2006.01)

(52) U.S. Cl.
CPC .......... *B26D 7/02* (2013.01); *A61B 17/12022* (2013.01); *F16H 25/122* (2013.01)

(58) Field of Classification Search
CPC .... B26D 7/02; F16H 25/122; A61B 17/12022
See application file for complete search history.

(56) References Cited

U.S. PATENT DOCUMENTS

| | | | | |
|---|---|---|---|---|
| 4,535,642 A * | 8/1985 | Ohmura | ................ | F16H 25/122 74/569 |
| 2013/0233108 A1* | 9/2013 | Chen | .................... | F16H 25/122 74/439 |
| 2014/0109703 A1* | 4/2014 | Howard | .................... | F41A 9/42 74/57 |
| 2017/0361386 A1* | 12/2017 | Lu | ........................... | F16H 25/12 |
| 2019/0301501 A1* | 10/2019 | Zhu | ....................... | F16H 57/032 |

FOREIGN PATENT DOCUMENTS

| | | |
|---|---|---|
| CN | 209549914 U | 10/2019 |
| CN | 212701649 U | 3/2021 |
| CN | 213837786 U | 7/2021 |

* cited by examiner

*Primary Examiner* — Terence Boes
(74) *Attorney, Agent, or Firm* — Nitin Kaushik

(57) ABSTRACT

Disclosed are a telescopic assembly and an occlusion mechanism. The telescopic assembly includes a rotating shaft, a telescopic piece, and a connecting piece; two spiral orbits extending in an axis direction are disposed on the circumferential side of the rotating shaft, and the spiral orbits are rotatably intersected with each other and communicate on tail ends to form a closed orbit; the telescopic piece sleeves around the rotating shaft; the connecting piece is movably connected to the telescopic piece, and the other end of the connecting piece moves in a spiral orbit groove all the time during movement; and with the rotation of the rotating shaft, the connecting piece drives the telescopic piece to do reciprocating movement along an axis so that the automatic telescopic movement of the telescopic piece is achieved. The telescopic assembly pushes a first rocking bar and a second rocking bar to achieve an occlusion action.

8 Claims, 8 Drawing Sheets

TELESCOPIC ASSEMBLY AND OCCLUSION MECHANISM

CROSS-REFERENCE TO RELATED APPLICATIONS

The application claims priority to Chinese patent application No. 202221482927. X, filed on Jun. 14, 2022, the entire contents of which are incorporated herein by reference.

TECHNICAL FIELD

The present application relates to the technical field of health care products, in particular to a telescopic assembly and an occlusion mechanism.

BACKGROUND

An occlusion mechanism generally includes two occluding arms disposed oppositely, the two occluding arms are generally connected to a telescopic piece, and by means of the telescopic movement of the telescopic piece, the two occluding arms are angularly close to or away from each other to achieve an occlusion action. In related art, the telescopic movement of the telescopic piece is achieved manually, which causes incapability of better controlling an occlusion force and an automatic occlusion effect.

SUMMARY

Embodiments of the present application provide a telescopic assembly and an occlusion mechanism, by which the self-energization of a telescopic movement can be achieved, so that the efficiency of the telescopic movement is increased.

In a first aspect, embodiments of the present application provide a telescopic assembly, including:

a rotating shaft, spiral orbits extending in an axis direction being disposed on the circumferential side of the rotating shaft, the spiral orbits including a first spiral orbit and a second spiral orbit opposite to the first spiral orbit in rotation direction, the initial end of the first spiral orbit communicating with the tail end of the second spiral orbit, and the tail end of the first spiral orbit communicating with the initial end of the second spiral orbit;

a telescopic piece, the telescopic piece being located on one side of the rotating shaft and doing linear reciprocating movement in the axis direction; and a connecting piece, the connecting piece being located between the rotating shaft and the telescopic piece, one end of the connecting piece being movably connected to the telescopic piece, and the other end thereof being abutted with the spiral orbits.

In some of the embodiments, an extension groove is formed in the telescopic piece, the rotating shaft rotatably penetrates in the extension groove, and the axis of the extension groove and the axis of the rotating shaft are colinear.

In some of the embodiments, the extension lengths of the first spiral orbit and the second spiral orbit are the same, and the numbers of turns of the first spiral orbit and the second spiral orbit are the same.

In some of the embodiments, the telescopic assembly further includes an auxiliary mounting piece fixedly connected to the telescopic piece and provided with a via hole penetrating through the auxiliary mounting piece in an axial direction, the axis of the via hole and the axis of the extension groove are colinear, the rotating shaft movably penetrates in the via hole and the extension groove, a mounting hole is formed in the auxiliary mounting piece, and the mounting hole extends in a direction perpendicular to the axis direction H to communicate with the via hole; and the telescopic assembly further includes a clamping piece, the clamping piece is inserted and connected into the mounting hole, a positioning groove is formed in the side, close to the extension groove, of the clamping piece, and one end of the connecting piece is movably mounted in the positioning groove.

In some of the embodiments, the connecting piece includes a connecting shaft, one end of the connecting shaft is movably mounted in the positioning groove, the other end thereof is abutted with the spiral orbits; or the connecting piece includes a connecting shaft and an abutting piece, the abutting piece is disposed to be shaped like an arc having the consistent rotation angle with the spiral orbits and is abutted with the bottoms of the spiral orbits, one end of the connecting shaft is movably mounted in the positioning groove, and the other end thereof is fixedly connected to the abutting piece.

In some of the embodiments, the auxiliary mounting piece is provided with a positioning hole, and the positioning hole penetrates through the auxiliary mounting piece in the axis direction H and communicates with the mounting hole;

the clamping piece is provided with a limiting hole, the limiting hole penetrates through a clamping piece in the axis direction H, and the axis of the positioning hole and the axis of the limiting hole are colinear; and the telescopic assembly further includes a positioning pin, and the positioning pin sequentially penetrates in the positioning hole and the limiting hole.

In some of the embodiments, the clamping piece is provided with a projection, a groove is formed in a position, corresponding to the projection, on the inner wall surface of the via hole, and the projection is located in the groove; or the inner wall of the via hole is provided with a projection, a groove is formed in a position, corresponding to the projection, on the clamping piece, and the projection is located in the groove.

In a second aspect, embodiments of the present application provide an occlusion mechanism, including:

a first rocking bar including a first connecting end and a first occluding end;

a second rocking bar including a second connecting end and a second occluding end; and the above-mentioned telescopic assembly;

wherein both of the first connecting end and the second connecting end are movably connected to the telescopic piece, and the telescopic piece does reciprocating movement in the axis direction so that the first occluding end is close to or away from the second occluding end.

In some of the embodiments, the occlusion mechanism includes a housing;

the first rocking bar includes a first rocking arm and a second rocking arm connected to the first rocking arm, the first rocking arm is provided with the first connecting end, the second rocking arm is provided with the first occluding end, and a position where the first rocking arm is connected to the second rocking arm is rotatably connected to the housing; and the second rocking bar includes a third rocking arm and a fourth rocking arm connected to the third rocking arm, the third rocking arm is provided with the second connecting end, the fourth rocking arm is provided with the second occluding end, and a position where the third rocking arm is connected to the fourth rocking arm is rotatably connected to the housing.

In some of the embodiments, the occlusion mechanism further includes:

a first connecting shaft, the axis of the first connecting shaft being perpendicular to the axis direction, one end of the first connecting shaft being fixedly connected to the telescopic piece, a first sleeving hole being formed in the end, close to the telescopic piece, of the first rocking arm, and the first rocking arm movably penetrating in the first sleeving hole;

a second connecting shaft, the axis of the second connecting shaft and the first connecting shaft being colinear, the first end of the second connecting shaft being fixedly connected to the telescopic piece, a second sleeving hole being formed in the end, close to the telescopic piece, of the second rocking arm, and the third rocking arm movably penetrating in the second sleeving hole;

or, the occlusion mechanism includes a first abutting column and a second abutting column, the telescopic piece being provided with a first abutting groove and a second abutting groove respectively along two opposite sides perpendicular to the axis direction, one end of the first abutting column being fixedly connected to the first rocking arm, the other end thereof being located in the first abutting groove, one end of the second abutting column being fixedly connected to the third rocking arm, and the other end thereof being located in the second abutting groove.

Based on the telescopic assembly and the occlusion mechanism in the embodiments of the present application, the first spiral orbit and the second spiral orbit communicate end to end to form a closed orbit; the connecting piece may be abutted with the bottom walls of the first spiral orbit and the bottom wall of the second spiral orbit; and with the rotation of the rotating shaft, the telescopic piece movably connected to the connecting piece may do reciprocating movement in the axis direction, and then, the automatic telescopic movement of the telescopic piece is achieved, so that the efficiency of the telescopic movement is increased. Then, the telescopic assembly pushes the first rocking bar and the second rocking bar to achieve an occlusion action so that an effect of simulating automatic occlusion of a mouth is achieved in a health care product.

BRIEF DESCRIPTION OF DRAWINGS

To describe the technical solutions in the embodiments of the present application or the prior art more clearly, the accompanying drawings required for describing the embodiments or the prior art will be briefly introduced below. Apparently, the accompanying drawings in the following description show only some embodiments of the present application, and the skill in the art may still derive other accompanying drawings from these accompanying drawings without creative efforts.

Figure 1:
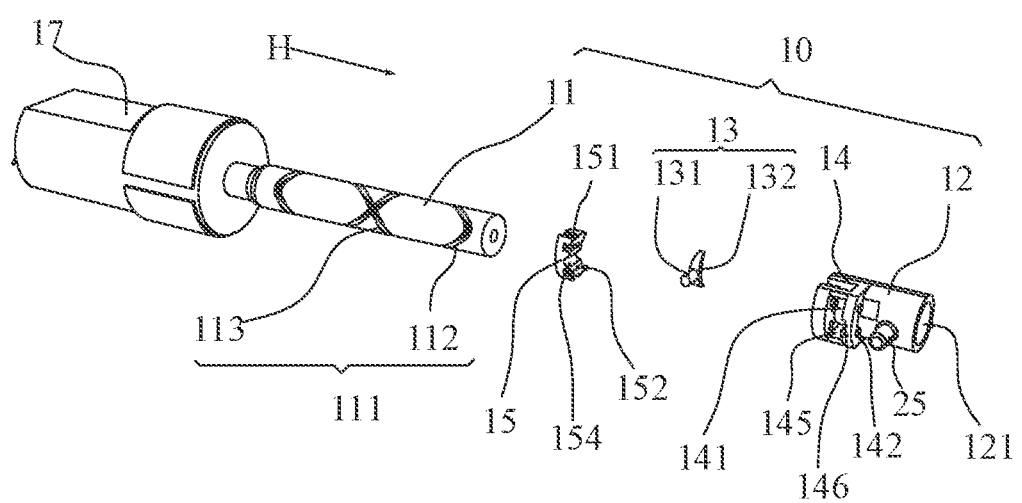
FIG. 1 is a schematic structural view showing a telescopic assembly in an embodiment of the present application.

REFERENCE NUMERALS IN THE ACCOMPANYING DRAWINGS 10, telescopic assembly;
11, rotating shaft; 111, spiral orbit; 112, first spiral orbit; 1121, first side wall; 1122, second side wall; 1123, first bottom wall; 113, second spiral orbit; 1131, third side wall; 1132, fourth side wall; 1133, second bottom wall;
12, telescopic piece; 121, extension groove;
13, connecting piece; 131, connecting shaft; 132, abutting piece;
14, auxiliary mounting piece; 141, via hole; 142, positioning hole; 145, mounting hole; 146, second groove;
15, clamping piece; 151, positioning projection; 152, limiting hole; 154, first groove;
17, driving piece;
21, first rocking bar; 211, first connecting end; 212, first occluding end; 213, first rocking arm; 2131, first sleeving hole; 214, second rocking arm; 215, first via hole;
22, second rocking bar; 221, second connecting end; 222, second occluding end; 223, third rocking arm; 2231, second sleeving hole; 224, fourth rocking arm; 225, second via hole;
23, housing;
25, second connecting shaft; 26, first stationary shaft; 27, second stationary shaft;
H, axis direction; A, first point; B, second point.

DETAILED DESCRIPTION OF THE INVENTION

In order to make objectives, technical solutions and advantages of the present application clearer and more understandable, the present application will be further described in detail below with reference to the accompanying drawings and the embodiments. It should be understood that the specific embodiments described herein are merely intended to explain the present application, rather than to limit the present application.

In related art, an occlusion mechanism generally includes two occluding arms disposed oppositely, and the two occluding arms are angularly close to or away from each other to achieve an occlusion action. The occlusion mechanism is limited by a mechanical structure, which causes the problems of smaller occlusion force and poor automatic occlusion effect, and thus, demands of users cannot be met.

Figure 2:
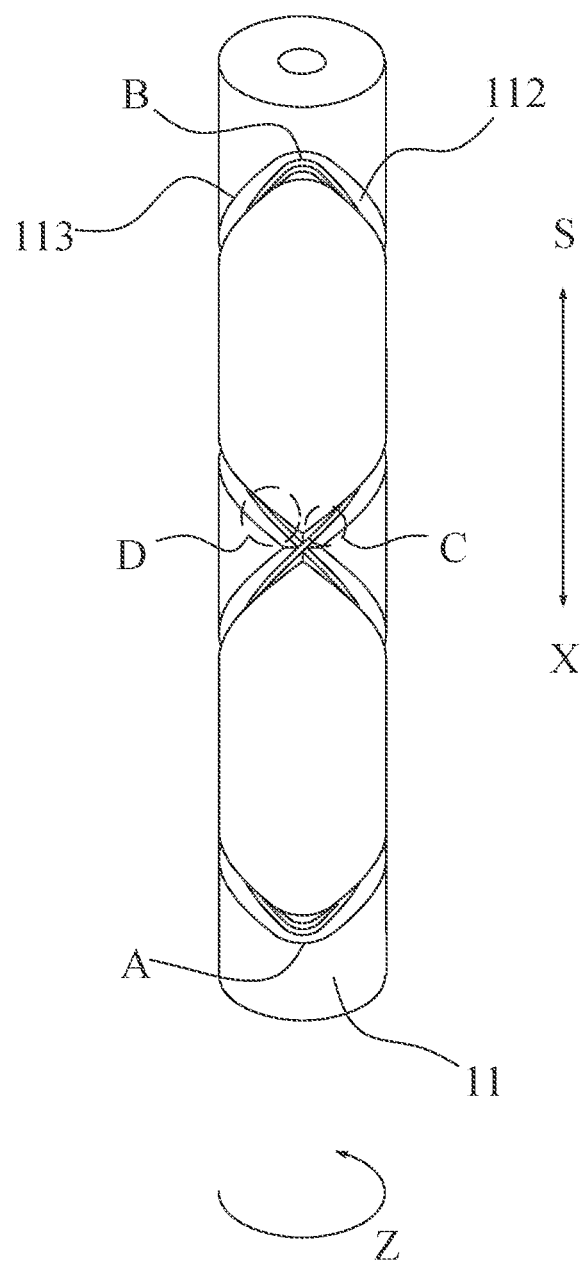
FIG. 2 is a schematic structural view showing a rotating shaft in an embodiment of the present application.

In order to solving the above-mentioned problems, referring to FIG. 1 to FIG. 2, in a first aspect, the present application provides a telescopic assembly 10. The telescopic assembly 10 includes a rotating shaft 11, a telescopic piece 12, and a connecting piece 13.

The rotating shaft 11 may be columnar, spiral orbits 111 are disposed on the circumferential side of the rotating shaft 11, and the spiral orbits 111 extend in an axis direction H.

The spiral orbits 111 have depths from the outer wall surface of the rotating shaft 11 to the central axis direction H, then, the sections of the spiral orbits 111 may be arc-shaped, U-shaped and the like in a direction perpendicular to extension directions of the spiral orbits 11. In the present application, the shapes of the sections of the spiral orbits 111 are not limited and can be set according to actual demands.

The spiral orbits 111 may includes a first spiral orbit 112 and a second spiral orbit 113, the first spiral orbit 112 is opposite to the second spiral orbit 113 in rotation direction, the initial end of the first spiral orbit 112 communicates with the tail end of the second spiral orbit 113, with a communication point being marked as a first point A, and the tail end of the first spiral orbit 112 communicates with the initial end of the second spiral orbit 113, with a communication point being marked as a second point B, so that the first spiral orbit 112 and the second spiral orbit 113 communicate end to end to form a closed orbit.

The telescopic piece 12 is located on the side, in the axis direction H, of the rotating shaft 11, the connecting piece 13 is located between the rotating shaft 11 and the telescopic piece 12, one end of the connecting piece 13 is movably connected to the telescopic piece 12, and the other end thereof is abutted with the spiral orbits 111; with the rotation of the rotating shaft 11, the end, abutted with the spiral orbits 111, of the connecting piece 13 moves along the spiral orbits; and meanwhile, the first spiral orbit 112 is opposite to the second spiral orbit 113 in rotation direction, and thus, the telescopic piece 12 may do reciprocating telescopic movement in the axis direction H.

The connecting piece 13 is provided with a connecting end (unshown in the figures) and an abutting end (unshown in the figures), the connecting end is movably connected to the telescopic piece 12, the abutting end is abutted with the bottoms of the spiral orbits 111, and therefore, when the abutting end is abutted with the first spiral orbit 112 and the second spiral orbit 113, with the variation of the rotation angles of the first spiral orbit 112 and the second spiral orbit 113, the connecting end may rotate at multiple angles relative to the telescopic piece 12, and then, it can be ensured that the abutting end does reciprocating movement in the spiral orbits 111.

It needs to be noted that the connecting piece 13 may movably connected to the telescopic piece 12 in a manner such as a ball head connecting shaft or a universal shaft, which is not limited in the present application and can be set according to actual demands.

Figure 3:
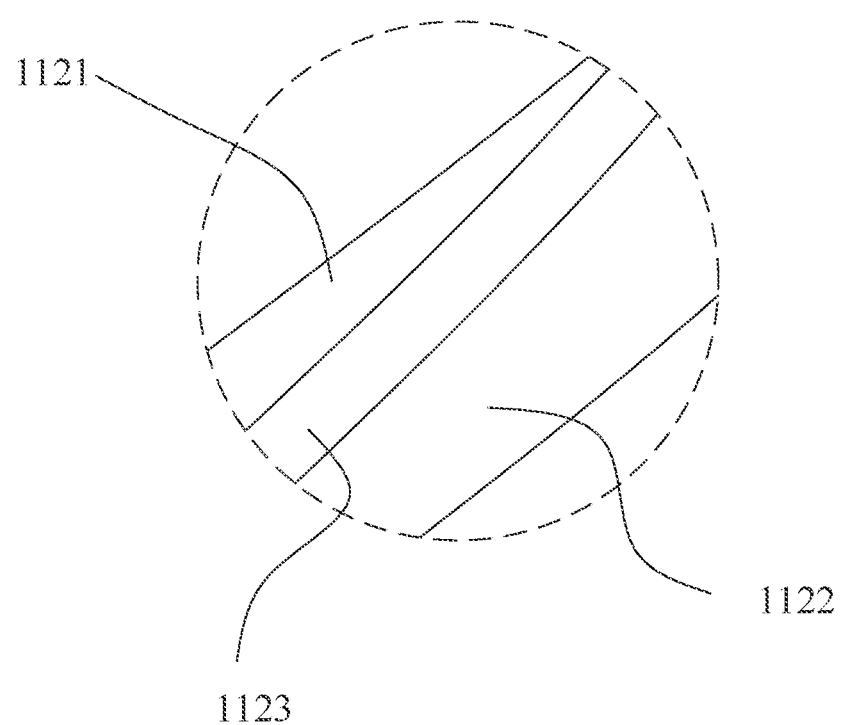
FIG. 3 is a schematic enlarged view showing a part C in FIG. 2.

Referring to FIG. 2 to FIG. 3, the sections of the spiral orbits 111 may be U-shaped, the first spiral orbit 112 may be a left-handed rotation orbit and may include a first side wall 1121, a second side wall 1122, and a first bottom wall 1123 configured to connect the first side wall 1121 and the second side wall 1122, the first side wall 1121 and the second side wall 1122 are disposed oppositely, and the abutting end of the connecting piece 13 may be abutted with the first bottom wall 1123. With the rotating shaft 11 rotating in a Z-axis direction (the Z-axis direction is a direction of rotation in the axis direction H) as an example, when the rotating shaft 11 rotates along a Z axis, the abutting end of the connecting piece 13 is pressed by the first side wall 1121 to move along the left-handed rotation orbit in a direction X (the direction X is parallel to the axis direction H), and then, with the rotation of the rotating shaft 11 along the Z axis, the abutting end of the connecting piece 13 moves to the first point A; at the moment, due to inertia, the abutting end of the connecting piece 13 may move to the second spiral orbit 113 and may be abutted with the bottom wall of the second spiral orbit 113.

Figure 4:
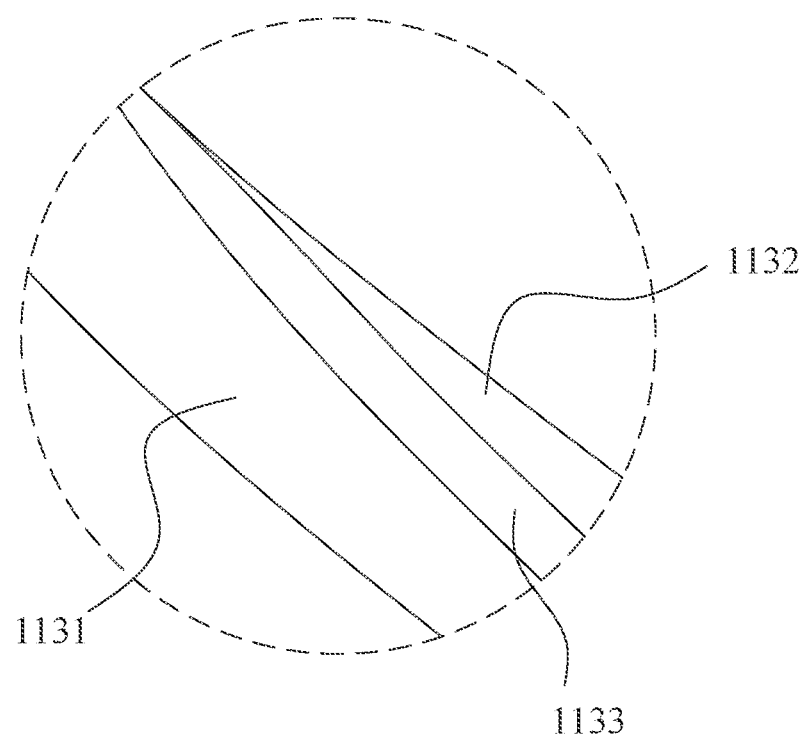
FIG. 4 is a schematic enlarged view showing a part D in FIG. 2.

Referring to FIG. 4 and combining with FIG. 2, the second spiral orbit 113 may be a right-handed rotation orbit opposite to the first spiral orbit 112 in rotation direction and may include a third side wall 1131, a fourth side wall 1132, and a second bottom wall 1133 configured to connect the third side wall 1131 and the fourth side wall 1132, the third side wall 1131 and the fourth side wall 1132 are disposed oppositely, and the abutting end of the connecting piece 13 may be abutted with the second bottom wall 1133. The abutting end of the connecting piece 13 moves to the second bottom wall 1133, the rotating shaft 11 rotates in the Z-axis direction, the abutting end of the connecting piece 13 is supported by the third side wall 1131 to move along the right-handed rotation orbit in a direction S (the direction S is opposite to the direction X), and then, with the rotation of the rotating shaft 11 along the Z axis, the abutting end of the connecting piece 13 moves to the second point B; at the moment, due to inertia, the abutting end of the connecting piece 13 may move to the first bottom wall 1123 of the first orbit and may be abutted with the bottom wall 1123.

With the rotation of the rotating shaft 11 along the Z axis, the butting end of the connecting piece 13 may do reciprocating movement between the first point A and the second point B in the axis direction H, the connecting end of the connecting piece 13 is movably connected to the telescopic piece 12, and then, the connecting piece 13 may drive the telescopic piece 12 to do telescopic movement in the axis direction H, so that the telescopic piece 12 does regular reciprocating movement in the axis direction H.

Further, arc processing may be performed on the first point A and the second point B to ensure that the abutting end of the connecting piece 13 may be switched between the first spiral orbit 112 and the second spiral orbit 113 relatively smoothly and further ensure that the telescopic piece 12 may does regular reciprocating movement in the axis direction H, so that the automatic telescopic movement of the telescopic piece 12 is achieved.

It needs to be noted that the rotating shaft 11 rotates unidirectionally, the rotation of the rotating shaft 11 may be driven by a driving piece 17 which may be a motor, and one end of the rotating shaft 11 may be fixedly connected to the motor so that the motor drives the rotating shaft 11 to rotate. In the present application, the type of the driving piece 17 is not limited and can be set according to actual demands.

Further, when the abutting end of the connecting piece 13 is abutted with the spiral orbits 111, the first side wall 1121 and the third side wall 1131 apply acting forces to the abutting end of the connecting piece 13, meanwhile, the abutting end of the connecting piece 13 may also apply a counter-acting force to the first side wall 1121 or the third side wall 1131, the distance from the telescopic piece 13 to the rotating shaft 11 is increased, which makes the abutting end of the connecting piece 13 separated from the bottom walls of the spiral orbits 111.

In order to prevent the abutting end of the connecting piece 13 from being separated from the bottom walls of the spiral orbits 111, an extension groove 121 may be formed in the telescopic piece 12, the section, in a direction perpendicular to the axis direction H, of the extension groove 121 is circular, the rotating shaft 11 may rotatably penetrate in the extension groove 121, and the axis of the extension groove 121 and the axis of the rotating shaft 11 are colinear. Further, due to the limitation of the inner side wall of the extension groove 121, the abutting end of the connecting piece 13 may still be located in the spiral orbits 111 even if the first side wall 1121 or the third side wall 1131 is acted by the counter-acting force of the abutting end of the connecting piece 13.

It needs to be noted that the diameter of a circle of the section, in a direction perpendicular to the axis direction H, of the extension groove 121 is a first diameter, the diameter of a circle of the section, in a direction perpendicular to the axis direction H, of the rotating shaft 11 is a second diameter, the first diameter is greater than the second diameter, so that the rotating shaft 11 may movably penetrate in the extension groove 121. In the present application, the values of the first diameter and the second diameter are not limited and can be set according to actual demands.

In some embodiments, the telescopic assembly 10 may also include a limiting piece (unshown in the figures), the limiting piece may be set to be strip-shaped and extend in the axis direction H, the telescopic piece 12 may be slidably connected to the limiting piece, which are similar to a screw and nut pair structure. Specifically, the position of the limiting piece is fixed relative to the rotating shaft 11 so that the distance from the limiting piece to the rotating shaft 11 is a fixed value; then, as the distance from the limiting piece to the rotating shaft 11 is fixed, the abutting end of the connecting piece 13 may still be located in the spiral orbits 111 even if the first side wall 1121 or the third side wall 1131 is acted by the counter-acting force of the abutting end of the connecting piece 13; and then, the situation that the telescopic piece 12 rotates with the rotation of the spiral orbits 111 can be avoided, so that the telescopic piece 12 does linear reciprocating movement in a direction limited by the limiting piece.

Further, with reference to FIG. 2, the extension lengths of the first spiral orbit 112 and the second spiral orbit 113 are the same, so that the distance of the telescopic piece 12 from the first point A to the second point B in the axis direction H is the same as the distance from the second point B to the first point A, and then, the reciprocating distance of the telescopic piece 12 in the axis direction H is the same. The distance from the first point A to the second point B is the same, and the numbers of turns of the first spiral orbit 112 and the second spiral orbit 113 are the same, which ensures that the movement speed of the telescopic piece 12 from the first point A to the second point B is the same as the movement speed thereof from the second point B to the first point A, and then, the uniformity of the reciprocating movement of the telescopic piece 12 along the rotating shaft 11 can be improved.

Figure 5:
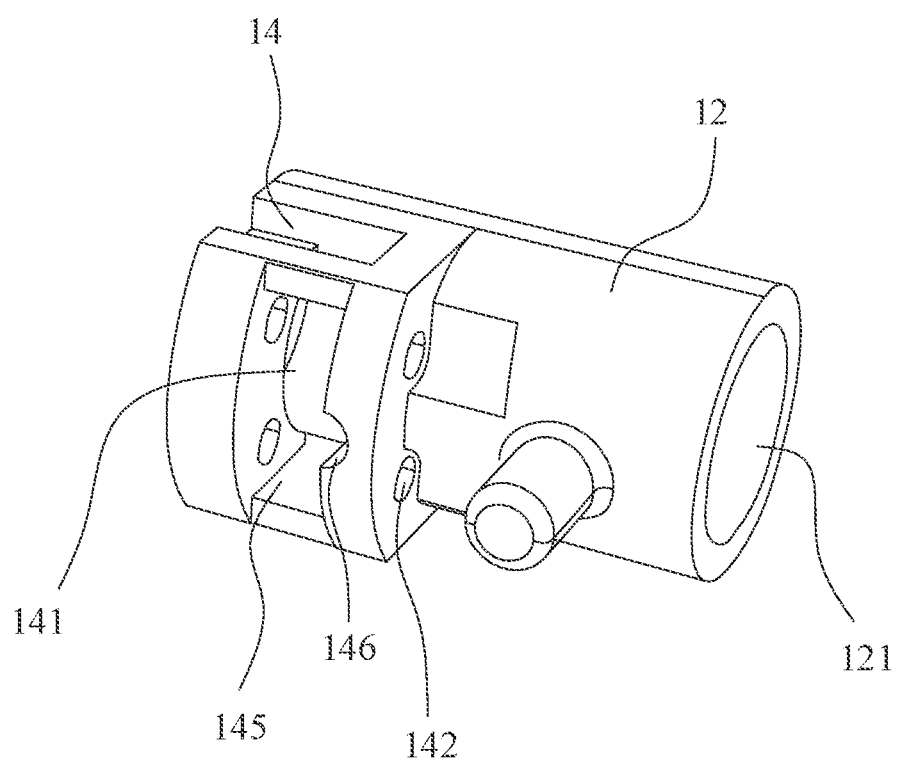
FIG. 5 is a schematic structural view showing that a telescopic piece is matched with an auxiliary mounting piece in an embodiment of the present application.

Further, referring to FIG. 5 and combining with FIG. 1, the telescopic assembly 10 further includes an auxiliary mounting piece 14 fixedly connected to the telescopic piece 12 in a manner which may be bonding or clamping. In some embodiments, the auxiliary mounting piece 14 may also be integrated with the telescopic piece 12. In the present application, the specific connection manner is not limited and can be set according to actual demands.

With reference to FIG. 1, the auxiliary mounting piece 14 is configured to fix the connecting piece 13 between the rotating shaft 11 and the inner wall of the extension groove 121. Specifically, the auxiliary mounting piece 14 is provided with a via hole 141 penetrating through the auxiliary mounting piece 14 in the axis direction H, the axis of the via hole 141 and the axis of the extension groove 121 are colinear, the rotating shaft 11 movably penetrates in the via hole 141 and the extension groove 121, and then, the rotating shaft 11 may penetrate in the via hole 141 to enter the extension groove 121. It needs to be noted that the diameter D3, in a direction perpendicular to the axis, of the via hole 141 is equal to or greater than the diameter D1 of a circle of the section, in a direction perpendicular to the axis direction H, of the extension groove 121, so that the rotating shaft 11 penetrates in the via hole 141 to enter the extension groove 121.

In order to facilitate mounting and fixing the connecting piece 13, a mounting hole 145 is formed in the auxiliary mounting piece 14, and the mounting hole 145 extends in a direction perpendicular to the axis direction H to communicate with the via hole 141; and the telescopic assembly 10 further includes a clamping piece 15, and the clamping piece 15 is inserted and connected into the mounting hole 145.

It needs to be noted that the section, in a direction perpendicular to the axis direction H, of the mounting hole 145 may be of a first rectangle, the section, in a direction perpendicular to the axis direction H, of the clamping piece 15 may also be of a second rectangle, the length and width of the first rectangle are greater than the length and width of the second rectangle, so that the clamping piece 15 may penetrate in the mounting hole 145 in the direction perpendicular to the axis direction H. In the present application, the lengths and widths of the first rectangle and the second rectangle are not specifically limited and can be set according to actual demands.

In some embodiments, the section, in the direction perpendicular to the axis direction H, of the mounting hole 145 may also be circular or polygonal and the like, and the shape of the section of the clamping piece 15 is similar to the shape of the section of the mounting hole 145. In the present application, the shapes of the sections of the mounting hole 145 and the clamping piece 15 are not limited and can be set according to actual demands.

Further, a positioning hole 142 is formed in part, projecting out of the telescopic piece 12, of the auxiliary mounting piece 14, and the positioning hole 142 penetrates through the auxiliary mounting piece 14 in the axis direction H and communicates with the via hole 141; the clamping piece 15 is provided with a limiting hole 152, the limiting hole 152 penetrates through a clamping piece in the axis direction H, the axis of the positioning hole 142 and the axis of the limiting hole 152 are colinear, and the shape of the section of the positioning hole 142 is similar to the shape of the section of the limiting hole 152; and the telescopic assembly 10 further includes a positioning pin (unshown in the figures), the positioning pin sequentially penetrates in the positioning hole 142 and the limiting hole 152, and then, the clamping piece 15 may be fixed in the mounting hole 145.

It needs to be noted that the section, in a direction perpendicular to the axis, of the positioning hole 142 may be circular or polygonal and the like. In the present application, the shape of the section of the positioning hole 142 is not limited and can be specifically set according to actual demands.

With reference to FIG. 1, the connecting piece 13 may be a connecting shaft 131, one end of the connecting shaft 131 is movably mounted in the positioning groove, and the other end thereof is abutted with the spiral orbits 111; and the connecting piece 13 may also include a connecting shaft 131 and an abutting piece 132, the abutting piece 132 is disposed to be shaped like an arc having the consistent rotation angle with the spiral orbits 111 and is abutted with the bottoms of the spiral orbits 111, one end of the connecting shaft 131 is movably mounted in the positioning groove, and the other end thereof is fixedly connected to the abutting piece 132.

It needs to be noted that two ends of the abutting piece 132 may be set to be sloped (unshown in the figures), so that the abutting piece 132 moves in the first spiral orbit 112 and the second spiral orbit 113.

Further, a first groove 154 is formed in the side, close to the inner side wall of the mounting hole 145, of the clamping piece 15, a second groove 146 is formed in a position, corresponding to the first groove 154, on the inner side wall of the mounting hole 145, and the first groove 154 and the second groove 146 are correspondingly covered to form a positioning hole (unshown in the figures).

The connecting piece 13 includes the connecting shaft 131 and the abutting piece 132, the first groove 154 and the second groove 146 may also be covered to form the positioning hole, the connecting shaft 131 may movably penetrate in the positioning hole, the abutting piece 132 is connected to one end of the connecting shaft 131, and the abutting piece 132 is located on one end of the connecting shaft 131, so that the connecting shaft 131 may move in a through hole due to the limitation of the abutting piece 132.

In some embodiments, the first groove 154 and the second groove 146 may also be correspondingly covered to form a positioning groove (unshown in the figures). When the connecting piece 13 includes the connecting shaft 131, one end of the connecting shaft 131 is inserted in the positioning groove and may be abutted with the bottom of the positioning groove, and then, the connecting shaft 131 may move in the positioning groove.

Further, in order to further improve the firmness of connection between the clamping piece 15 and the auxiliary mounting piece 14, the outer side wall of the clamping piece 15 may also be provided with a positioning projection 151, a positioning groove (unshown in the figures) is formed in a position, corresponding to the positioning projection 151, on the inner wall surface of the via hole 141, the positioning projection 151 is located in the positioning groove, and the positioning projection is buckled into the positioning groove, and then, the clamping piece 15 is fixedly connected to the auxiliary mounting piece 14, that is, the clamping piece 15 is buckled with or separated from the auxiliary mounting piece 14 by pulling or insertion, so that fixed connection therebetween is facilitated, and the convenience of connection therebetween is also improved.

In some embodiments, the inner wall of the via hole 141 may also be provided with a projection (unshown in the figures), a groove (unshown in the figures) may also be formed in a position, corresponding to the projection, on the clamping piece 15, and the projection is located in the groove, so that buckled connection between the clamping piece 15 and the auxiliary mounting piece 14 is achieved. In the present application, the manner of connection between the clamping piece 15 and the auxiliary mounting piece 14 is not limited and can be set according to actual demands.

Figure 6:
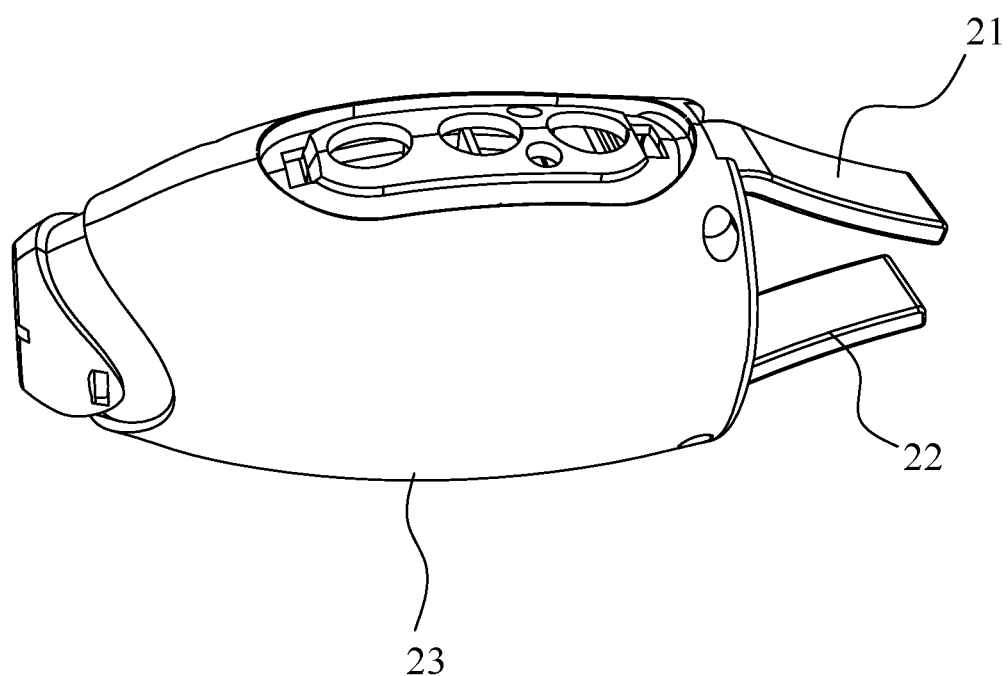
FIG. 6 is a schematic view showing an integral structure of an occlusion mechanism in an embodiment of the present application.
Figure 7:
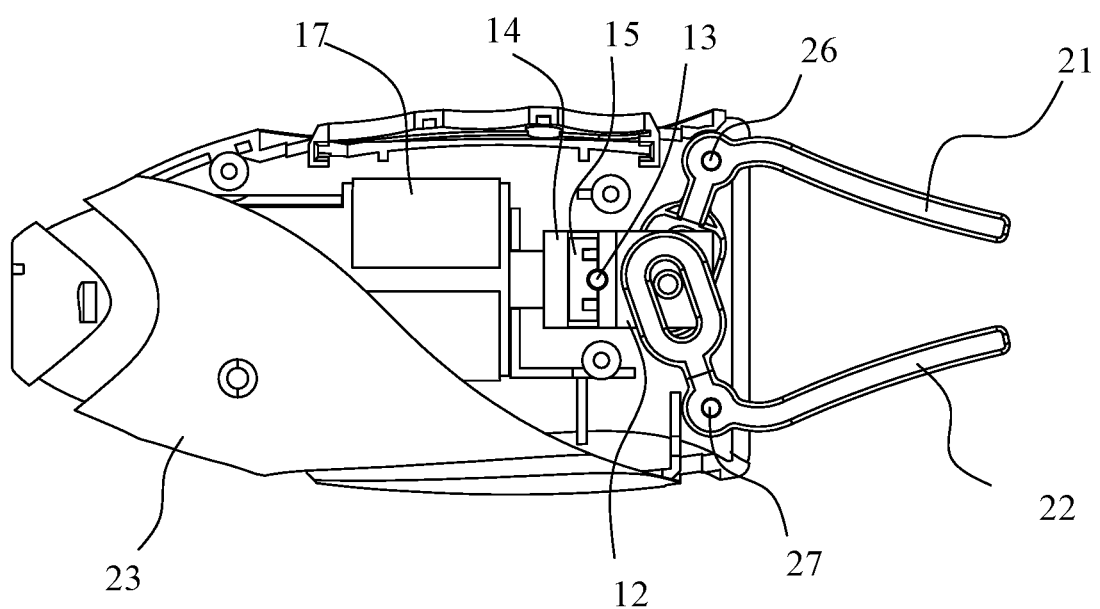
FIG. 7 is a schematic view showing a partial sectional structure of an occlusion mechanism in an embodiment of the present application.
Figure 8:
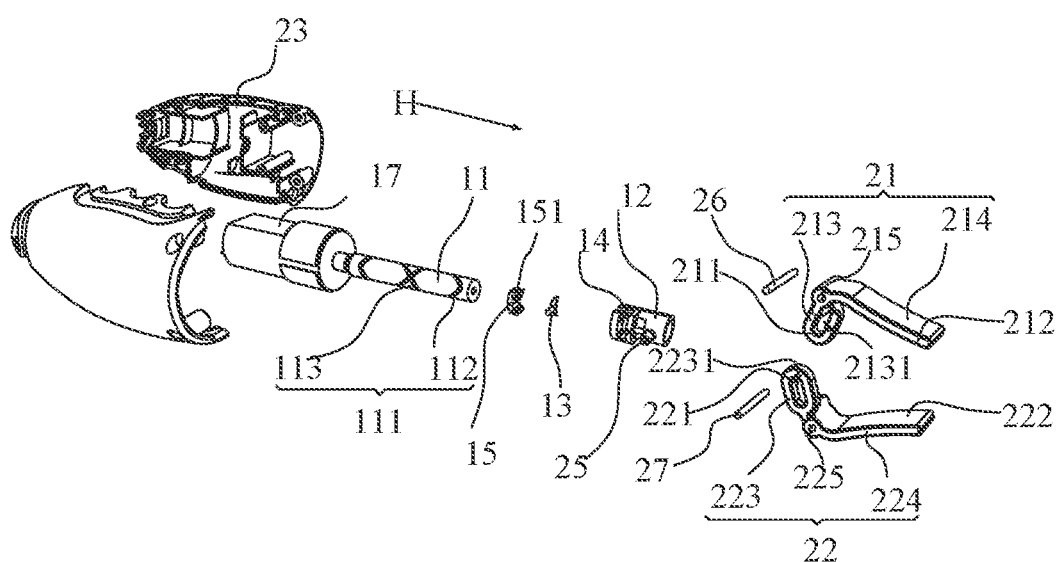
FIG. 8 is a schematic view showing an exploded structure of an occlusion mechanism in an embodiment of the present application.

In a second aspect, referring to FIG. 6 to FIG. 8, the present application provides an occlusion mechanism. The occlusion mechanism may include a first rocking bar 21, a second rocking bar 22, and the above-mentioned telescopic assembly 10.

The first rocking bar 21 may include a first connecting end 211 and a first occluding end 212, and the second rocking bar may also include a second connecting end 221 and a second occluding end 222. Both of the first connecting end 211 and the second connecting end 221 are movably connected to the telescopic piece 12, and the telescopic piece 12 does reciprocating movement in the axis direction H so that the first occluding end is close to or away from the second occluding end to achieve an occlusion action, and then, an object put between the first occluding end 212 and the second occluding end 222 can be occluded.

Further, the occlusion mechanism further includes a housing 23 covering the circumferential side of the telescopic assembly 10, the housing 23 is provided with a telescopic region along an axis, so that the telescopic assembly 10 may do telescopic movement in the housing 23, and influences of external factors on the telescopic assembly 10 can be avoided to protect the telescopic assembly.

Specifically, referring to FIG. 8, the first rocking bar 21 may include a first rocking arm 213 and a second rocking arm 214 connected to the first rocking arm 213, the first rocking arm 213 is provided with the first connecting end 211, the second rocking arm 214 is provided with the first occluding end 212, and the end, away from the first connecting end 211, of the first rocking arm 213 is fixedly connected to the end, away from the first occluding end 212, of the second rocking arm 214 in a manner such as bonding or integrally molding, which can be specifically set according to actual demands.

An included angle is set between the first rocking arm 213 and the second rocking arm 214, and a position where the first rocking arm 213 is connected to the second rocking arm 214 is rotatably connected to the housing 23. With the reciprocating movement of the telescopic piece 12 in the axis direction H, the first rocking arm 213 may be driven to rotate, and then, the second rocking arm 214 fixedly connected to the first rocking arm 213 is driven to rotate.

With reference to FIG. 8, a first via hole 215 is formed in the position where the first rocking arm 213 is connected to the second rocking arm 214. The occlusion mechanism further includes a first stationary shaft 26, the axis of the first stationary shaft 26 is perpendicular to the axis direction H; moreover, the first stationary shaft 26 is fixedly mounted on the housing 23, the first via hole 215 sleeves the first stationary shaft 26, and thus, the rotatable connection between the position where the first rocking arm 213 is connected to the second rocking arm 214 and the housing 23 can be achieved.

It needs to be noted that the first stationary shaft 26 and the housing 23 may be connected in a manner such as bonding, threaded connection or integrally molding, which is not specifically limited in the present application and can be set according to actual demands.

The second rocking bar 22 includes a third rocking arm 214 and a fourth rocking arm 224 connected to the third rocking arm 223, the third rocking arm 223 is provided with the second connecting end 221, the fourth rocking arm 224 is provided with the second occluding end 222, and the end, away from the second connecting end 221, of the third rocking arm 223 is fixedly connected to the end, away from the second occluding end 222, of the fourth rocking arm 224 in a manner such as bonding or integrally molding, which can be specifically set according to actual demands.

An included angle is set between the third rocking arm 223 and the fourth rocking arm 224, and a position where the third rocking arm 223 is connected to the fourth rocking arm 224 is rotatably connected to the housing 23. With the reciprocating movement of the telescopic piece 12 in the axis direction H, the third rocking arm 223 may be driven to rotate, and then, the fourth rocking arm 224 fixedly connected to the third rocking arm 223 is driven to rotate.

A second via hole 225 is formed in the position where the third rocking arm 223 is connected to the fourth rocking arm 224. The occlusion mechanism further includes a second stationary shaft 27, the axis of the second stationary shaft 27 is perpendicular to the axis direction H; moreover, the second stationary shaft 27 is fixedly mounted on the housing 23, the second via hole 225 sleeves the second stationary shaft 27, and thus, the rotatable connection between the position where the third rocking arm 223 is connected to the fourth rocking arm 224 and the housing 23 can be achieved.

It needs to be noted that the second stationary shaft 27 and the housing 23 may be connected in a manner such as bonding, threaded connection or integrally molding, which is not specifically limited in the present application and can be set according to actual demands.

The occlusion mechanism further includes a first connecting shaft (unshown in the figures) and a second connecting shaft 25; the axis of the first connecting shaft is perpendicular to the axis direction H, one end of the first connecting shaft is fixedly connected to the telescopic piece 12, a first sleeving hole 2131 is formed in the end, close to the telescopic piece 12, of the first rocking arm 213, the first connecting shaft movably penetrates in the first sleeving hole 2131, and thus, the first rocking arm 213 may rotate around the first connecting shaft.

The axis of the second connecting shaft 25 is parallel to the first connecting shaft, the first end of the second connecting shaft 25 is fixedly connected to the telescopic piece 12, a second sleeving hole 2231 is formed in the end, close to the telescopic piece 12, of the third rocking arm 223, the second connecting shaft 25 movably penetrates in the second sleeving hole 2231, and thus, the third rocking arm 223 may rotate around the second connecting shaft 25.

It needs to be noted that the first sleeving hole 2131 may be set as a strip-shaped hole in an extension direction of the first rocking arm 213, the first connecting shaft may have more movement allowance in the first sleeving hole 2131, and thus, the flexibility of the first connecting shaft moving in the first sleeving hole 2131 can be improved; and the second sleeving hole 2231 may be set as a strip-shaped hole in an extension direction of the second rocking arm 214, the second connecting shaft 25 may have more movement allowance in the second sleeving hole 2231, and thus, the flexibility of the second connecting shaft 25 moving in the second sleeving hole 2231 can be improved. In some embodiments, the occlusion mechanism may include a first abutting column (unshown in the figures) and a second abutting column (unshown in the figures), the telescopic piece 12 is provided with a first abutting groove and a second abutting groove respectively along two opposite sides perpendicular to the axis direction H, one end of the first abutting column is fixedly connected to the first rocking arm 213, the other end thereof is located in the first abutting groove, one end of the second abutting column is fixedly connected to the third rocking arm 223, the other end thereof is located in the second abutting groove, and thus, the movable connection between each of the first rocking arm 213 and the third rocking arm 223 and the telescopic piece 12 is achieved.

It needs to be noted that in the present application, the manner of movable connection between each of the first rocking arm 213 and the second rocking arm 214 and the telescopic piece 12 is not limited and can be limited according to actual demands.

With the reciprocating movement of the telescopic piece 12 in the axis direction H, both of the first connecting shaft and the second connecting shaft 25 may be fixedly connected to the telescopic piece 12, the telescopic piece 12 may drive the first rocking arm 213 to rotate by means of the first connecting shaft, and meanwhile, the telescopic piece 12 may also drive the third rocking arm 223 to rotate by means of the second connecting shaft 25; then, the second rocking arm 214 and the fourth rocking arm 224 may be driven to rotate, the second rocking arm 214 may be close to or away from the fourth rocking arm 224, and thus, the occlusion between the second rocking arm 214 and the fourth rocking arm 224 is achieved.

It needs to be noted that the longer the distance of reciprocating movement of the telescopic piece 12 is, the closer the first occluding end 212 is to the second occluding end 222, that is, the shorter the distance from the first occluding end 212 to the second occluding end 222 is, the greater the occlusion force for the object put between the first occluding end 212 and the second occluding end 222 is.

Then, the extension lengths of both of the first spiral orbit 112 and the second spiral orbit 113 may be adjusted to increase the rotation angles of the third rocking arm 223 and the fourth rocking arm 224, the distance from the first occluding end 212 to the second occluding end 222 may be adjusted, and thus, the occlusion force between the second rocking arm 214 and the fourth rocking arm 224 may be increased.

The same or similar reference numerals in the accompanying drawings of the present embodiment correspond to the same or similar components. In the description of the present application, it should be understood that directional or positional relationships indicated by terms such as "upper", "lower", "left", and "right" are based on directional or positional relationships as shown in the accompanying drawings, and are only for the purposes of facilitating describing the present application and simplifying the description, rather than indicating or implying that the referred apparatus or element has to have a specific direction or be constructed and operated in the specific direction, and therefore, the terms for describing the positional relationships in the accompanying drawings are merely used for exemplary description, but cannot be regarded as limitations on the present patent. The ordinary skill in the art may understand the specific meanings of the above-mentioned terms according to specific conditions.

The above descriptions are merely preferred embodiments of the present application, but are not intended to limit the present application. Any modifications, equivalent replacements, improvements and the like made within the spirit and principle of the present application shall fall within the protective scope of the present application.

What is claimed is:

1. A telescopic assembly, comprising:
a rotating shaft, spiral orbits extending in an axis direction being disposed on the circumferential side of the rotating shaft, the spiral orbits comprising a first spiral orbit and a second spiral orbit opposite to the first spiral orbit in rotation direction, the initial end of the first spiral orbit communicating with the tail end of the second spiral orbit, and the tail end of the first spiral orbit communicating with the initial end of the second spiral orbit;
a telescopic piece, the telescopic piece being located on one side of the rotating shaft and doing linear reciprocating movement in the axis direction; and
a connecting piece, the connecting piece being located between the rotating shaft and the telescopic piece, one end of the connecting piece being movably connected to the telescopic piece, and the other end thereof being abutted with the spiral orbits; an occlusion mechanism, comprising a first rocking bar comprising a first connecting end and a first occluding end; a second rocking bar comprising a second connecting end and a second occluding end; wherein both of the first connecting end and the second connecting end are movably connected to the telescopic piece, and the telescopic piece does reciprocating movement in the axis direction so that the first occluding end is adjacent to or away from the second occluding end; then, the telescopic assembly pushes the first rocking bar and the second rocking bar to achieve an occlusion action so that an effect of simulating automatic occlusion of a mouth is achieved in the technical field of health care products.

2. The telescopic assembly of claim 1, wherein an extension groove is formed in the telescopic piece, the rotating shaft rotatably penetrates in the extension groove, and the axis of the extension groove and the axis of the rotating shaft are colinear.

3. The telescopic assembly of claim 1, wherein the extension lengths of the first spiral orbit and the second spiral orbit are the same, and the numbers of turns of the first spiral orbit and the second spiral orbit are the same.

4. The telescopic assembly of claim 2, further comprising:
an auxiliary mounting piece fixedly connected to the telescopic piece and provided with a via hole penetrating through the auxiliary mounting piece in an axial direction, the axis of the via hole and the axis of the extension groove being colinear, the rotating shaft movably penetrating in the via hole and the extension groove, a mounting hole being formed in the auxiliary mounting piece, and the mounting hole extending in a direction perpendicular to the axis direction to communicate with the via hole; and
the telescopic assembly further comprising a clamping piece, the clamping piece being inserted and connected into the mounting hole, a positioning groove being formed in the side, adjacent to the extension groove, of the clamping piece, and one end of the connecting piece being movably mounted in the positioning groove.

5. The telescopic assembly of claim 4, wherein the connecting piece comprises a connecting shaft, one end of the connecting shaft is movably mounted in the positioning groove, the other end thereof is abutted with the spiral orbits; or the connecting piece comprises a connecting shaft and an abutting piece, the abutting piece is disposed to be shaped like an arc having the consistent rotation angle with the spiral orbits and is abutted with the bottoms of the spiral orbits, one end of the connecting shaft is movably mounted in the positioning groove, and the other end thereof is fixedly connected to the abutting piece.

6. The telescopic assembly of claim 4, wherein
the auxiliary mounting piece is provided with a positioning hole, and the positioning hole penetrates through the auxiliary mounting piece in the axis direction and communicates with the mounting hole;
the clamping piece is provided with a limiting hole, the limiting hole penetrates through a clamping piece in the axis direction, and the axis of the positioning hole and the axis of the limiting hole are colinear; and
the telescopic assembly further comprises a positioning pin, and the positioning pin sequentially penetrates in the positioning hole and the limiting hole.

7. The occlusion mechanism of claim 1, wherein
the occlusion mechanism comprises a housing;
the first rocking bar comprises a first rocking arm and a second rocking arm connected to the first rocking arm, the first rocking arm is provided with the first connecting end, the second rocking arm is provided with the first occluding end, and a position where the first rocking arm is connected to the second rocking arm is rotatably connected to the housing; and
the second rocking bar comprises a third rocking arm and a fourth rocking arm connected to the third rocking arm, the third rocking arm is provided with the second connecting end, the fourth rocking arm is provided with the second occluding end, and a position where the third rocking arm is connected to the fourth rocking arm is rotatably connected to the housing.

8. The occlusion mechanism of claim 7, further comprising:
a first connecting shaft, the axis of the first connecting shaft being perpendicular to the axis direction, one end of the first connecting shaft being fixedly connected to the telescopic piece, a first sleeving hole being formed in the end, adjacent to the telescopic piece, of the first rocking arm, and the first rocking arm movably penetrating in the first sleeving hole;
a second connecting shaft, the axis of the second connecting shaft and the first connecting shaft being colinear, the first end of the second connecting shaft being fixedly connected to the telescopic piece, a second sleeving hole being formed in the end, adjacent to the telescopic piece, of the second rocking arm, and the third rocking arm movably penetrating in the second sleeving hole.

* * * * *